Nov. 29, 1938. R. L. BYRUM Plant Pat. 305
ROSE
Filed Feb. 11, 1938
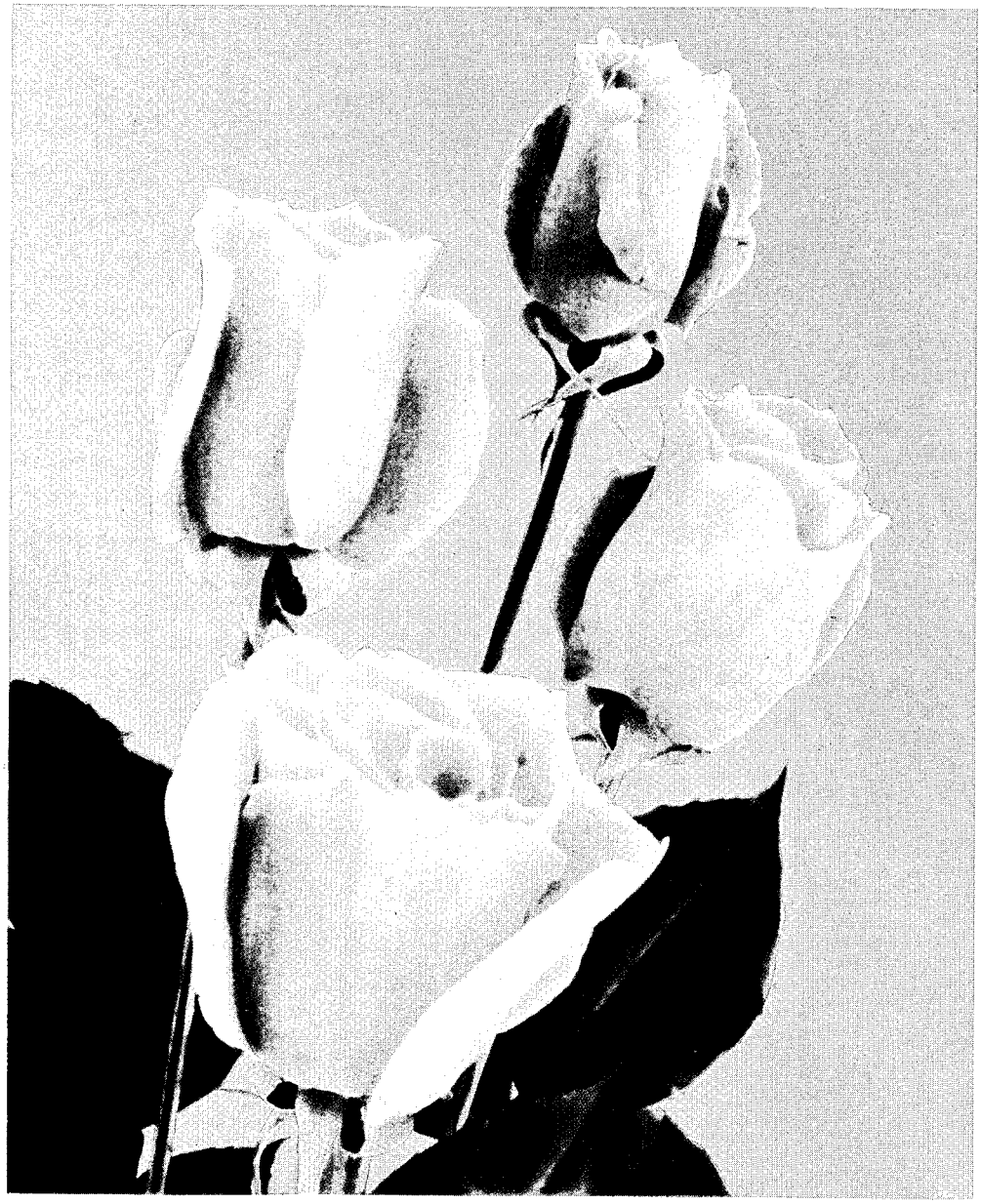
Inventor
Roy L. Byrum
By Robert Robb
Attorneys Patented Nov. 29, 1938

UNITED STATES PATENT OFFICE

305

ROSE

Roy L. Byrum, Richmond, Ind., assignor to Jos. H. Hill Company, Richmond, Ind.

Application February 11, 1938, Serial No. 190,112

1 Claim. (Cl. 47—61)

The present invention relates to a new and distinct variety of rose plant originated as the result of a definite effort to improve upon a rose, as yet an unnamed seedling, which in turn was the result of a cross between "Senior" (Plant Patent No. 2) as the pollen parent, and "De Luxe" as the seed parent.

While the flower of this unnamed seedling possessed a very desirable brilliant pink color, it had too few petals to warrant dissemination. Therefore, my primary object in view was to obtain a better petal characteristic, such as possessed by "Sweet Adeline" (Plant Patent No. 6) and at the same time overcome one of the undesirable characters of the last named variety. "Sweet Adeline" is a very difficult rose to propagate by grafting on Manetti stock, for I found that even after union was made, the scions would leave the manetti with the result of loss of many plants during blooming season.

In carrying out this invention, I crossed this unnamed seedling with "Sweet Adeline" and obtained the present rose, which has as its outstanding characteristics:—

(1) Distinctiveness of color and size of its blossoms;

(2) A better growing habit, greater productiveness per plant of cut flowers than its parents;

(3) An easy propagation character.

Asexual reproduction proves these characteristics to be fixed.

The original illustration shows the blossoms of this new variety in full color and substantially natural size and in four different stages of development from bud to full blown rose, and the following is a detailed description of the rose, color designations being in accordance with Ridgway's Color Standard:—

Parentage (seedling):

*Seed parent.*—$F_1$ seedling of Senior x De Luxe.

*Pollen parent.*—Sweet Adeline.

Classification:

*Botanic and commercial.*—Hybrid Tea.

*Flower*

Blooming habit:

Observations made in greenhouses of the Jos. H. Hill Company, Richmond, Indiana.

Recurrent—continuous.

Bud (before calyx breaks):

*Size.*—Large.

*Form.*—Long, pointed, with conspicuous neck; with foliaceous appendages on the surface of the bud; with slender, bristle-like foliaceous parts extending beyond the tip of the bud equal to ¼ of its length. Is not affected by wet or hot weather.

*Color.*—When sepals first divide—Rose Red (Plate XII). When petals begin to unfurl—changes gradually to Spinel Pink (Plate XVI). When half blown—Spinel Pink all over.

*Sepals.*—Smooth edge; curl back at bud stage.

*Calyx.*—Shape—apple; size—large; aspect—smooth; odor when rubbed—none.

*Peduncle.*—Length—long; aspect—slightly prickly; color—medium green; strength—stiff, heavy; opening—bud opens well.

Bloom:

*Size.*—Very large; average size when fully expanded—6 inches.

*Borne.*—Singly.

*Stems.*—Long, strong.

*Form.*—When first open—full; permanence—outer petals curl back slightly; retains its form to the end.

*Petalage.*—Double (full but open center); petals—very large; number of petals under normal conditions—21 to 25.

*Color.*—Spinel Pink; variegations—none; discoloration—holds color to end.

Petals:

*Texture.*—Thick, leathery.

*Appearance.*—Satiny.

*Form.*—Oval.

*Arrangement.*—Imbricated; petaloids in center—none.

*Persistence.*—Hang on.

*Fragrance.*—Slight; nature—Tea (average Hybrid Tea scent).

*Lasting Quality.*—On plant and as cut flower—very long.

Genital organs:

*Stamens, anthers.*—Medium; color—yellow; arrangement—regular around styles.

*Stamens, filaments (threads).*—Medium; color—Spinel Red.

*Pollen.*—Lemon Yellow.

*Styles.*—Bunched; uneven length; medium, thin.

*Stigmas.*—White.

*Ovaries.*—All enclosed in calyx.
*Hips.*—Size: medium—ovoid; shape: pear-shaped—yellow; very smooth; wall thick, fleshy.

Fruit:
Variety is fertile with its own pollen.
*Form.*—Round.
*Aspect.*—Smooth.
*Color at maturity.*—Orange.
*Sepals.*—Permanent, straight.

*Plant*

Form:
Bush.
Growth:
Vigorous; upright, compact.
Foliage:
*Leaves.*—Very heavy.
*Leaflets.*—Generally 5, sometimes 7. Shape—oval with apex acute—base round. Margin—simply irregularly serrate. Size—large. Quantity—abundant.
*Color.*—New foliage: upper side—light green edged with bronze; under side—light green. Old foliage: upper side—dark green; under side—light green.
*Shape.*—Oval pointed.
*Texture.*—Upper side—leathery; under side—rough. Ribs and veins—light impresed.
*Edge.*—serrated. Serration—single, small, sharp.
*Rachis.*—Medium with upper surface smooth, grooved. Upper side—reddish; under side—few prickles, green.
*Stipules.*—Short, smooth.
*Disease resistance.*—Resistant.

Wood:
*New wood.*—Color—light green, bronzy; bark—smooth.
*Old wood.*—Color—green; bark—smooth.

Thorns (divided into thorns, prickles, and short needles):
*Thorns.*—Quantity: on main stalks—ordinary; on laterals—few. Form—narrow, flat base; medium length; hooked slightly downward. Color when young—red. Position—irregular.
*Prickles.*—None.
*Short needles.*—None.

I claim:

A new and distinct variety of rose plant characterized as to novelty by the ease with which it may be propagated, the large productivity of blooms per plant, and the distinctive color and size of its blossoms, substantially as shown and described.

ROY L. BYRUM.